(12) United States Patent
Johnston

(10) Patent No.: US 7,092,092 B1
(45) Date of Patent: Aug. 15, 2006

(54) HAND-CARRIED LED POLARISCOPE

(75) Inventor: David W. Johnston, Kensington, NH (US)

(73) Assignee: Osram Sylvania Inc., Danvers, MA (US)

( * ) Notice: Subject to any disclaimer, the term of this patent is extended or adjusted under 35 U.S.C. 154(b) by 0 days.

(21) Appl. No.: 10/908,647

(22) Filed: May 20, 2005

(51) Int. Cl.
*G01J 4/00* (2006.01)
(52) U.S. Cl. .................................................. 356/366
(58) Field of Classification Search ................ None
See application file for complete search history.

(56) References Cited

U.S. PATENT DOCUMENTS

| | | | |
|---|---|---|---|
| 5,209,231 A | 5/1993 | Cote et al. ................ 128/633 |
| 5,671,301 A * | 9/1997 | Kupershmidt ................ 385/1 |
| 6,246,893 B1 | 6/2001 | Gobeli ........................ 600/318 |
| 6,718,201 B1 * | 4/2004 | Phipps et al. ................ 604/20 |
| 6,924,893 B1 | 8/2005 | Oldenbourg et al. ........ 356/369 |
| 2005/0094144 A1 * | 5/2005 | Gibbs et al. ................ 356/365 |

* cited by examiner

*Primary Examiner*—Tu T. Nguyen
(74) *Attorney, Agent, or Firm*—Robert F. Clark

(57) ABSTRACT

A polariscope that measures stress in glass and that is adapted to be hand-carried includes a lightweight, C-shaped housing with a sequential arrangement of a battery-powered LED light source, a first polarizer, a full wave plate at one distal end, and a second polarizer at a second distal end. The housing includes a hand-grip that houses a battery, where the battery is selectively connected to the LED light source with a switch carried on the hand-grip. The sequential arrangement of light source, first polarizer and full wave plate at the first distal end is less than two inches thick. The polariscope weighs less than two pounds and does not require an external power source.

12 Claims, 1 Drawing Sheet

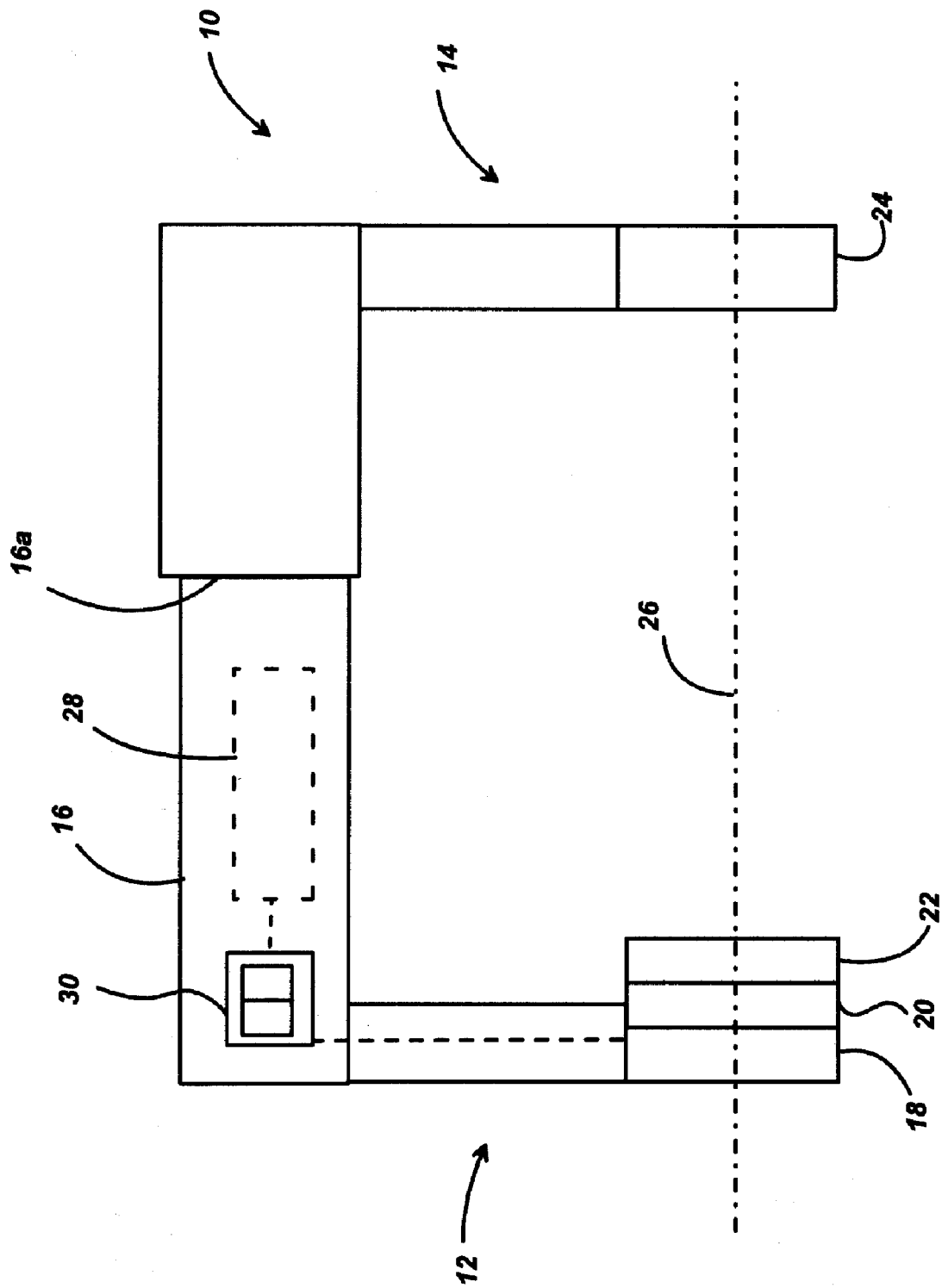

HAND-CARRIED LED POLARISCOPE

CROSS REFERENCE TO RELATED APPLICATION

This application is related to copending application Ser. No. 10/711,605 filed Sep. 28, 2004, which is hereby incorporated by reference.

BACKGROUND OF THE INVENTION

This invention is related to polariscopes, and more particularly to polariscopes that are portable.

A polariscope shows and qualitatively measures stress in glass and other photoelastic materials. When isotropic, photoelastic materials, such as glass and some plastics, are stressed, they become anisotropic. The anisotropy within the material makes the stressed areas birefringent. With a polariscope, one can determine the degree of anisotropy by observing the degree of birefringence, and determine a relative direction of tensile and compressive stress vectors. These can then be related qualitatively to the amount of stress within the material. A polariscope generally includes a light source, a first polarizer, a full wave plate and a second polarizer. The article to be tested is placed between the full wave plate and the second polarizer.

The above-cited application proposes an LED light source for a polarimeter instead of the commonly-used incandescent lamp. Although the incandescent lamp produces a smooth spectrum of white light, nearly 85% of the energy input to the lamp is converted to heat. This excessive heat causes damages to the polarizing film of the first polarizer that is adjacent to the lamp in the polarimeter. Over a relatively short time period, the damage to the film diminishes the ability of the polarimeter to accurately measure stress.

The LED light source in the above-cited application can also replace the compact fluorescent lamps that have been used in polarimeters to diminish the damage to the polarizing film from heat. However, the use of fluorescent lamps greatly increases the chance for chromatic aberrations. A failed lamp must be replaced with a reasonably exact duplicate otherwise the difference in the emission spectrum will shift the calibration of the polarimeter. In the case of fluorescent lamps, it is easy to make a mistake since the emission spectrum of a fluorescent lamp is a function of the phosphors used in its manufacture, e.g., there are several "colors" of white for commercial fluorescent lamps. Likely, the operator will be unaware of the color shift of the lamp and therefore not be able to compensate for it.

The manufacture of glass articles includes the controlled cooling of the glass to avoid generating stresses in the glass. A temperature difference within the glass as it cools through the glass transition range can cause stress in the glass. The intensity of the stress is directly related to the contraction properties of the glass and the intensity of the temperature difference. A polariscope can be used in a glass article manufacturing line to determine where alterations in the cooling process are needed to equalize the temperatures in the glass. Specifically, the hot glass article is removed from the line, typically while the line is in motion, and the glass is placed in the field of view of a polariscope. At some point in time, the glass article will exhibit birefringence (stress) indicating that the article is passing through the glass transition range. The time when the stress first appears must be measured accurately so the relative position of the manufacturing line can be determined. This operation can be dangerous for the operator and tends to be less accurate than desired.

Heretofore, the use of an incandescent or fluorescent lamp polariscope on a glass article manufacturing line without removing the glass article from the line has not been practical because of the size and weight of the polariscope. A typical "portable" polariscope is 8" in diameter, 14" high, weighs 11 pounds, is connected to a cumbersome electrical cable, and has a light source that is about 10" deep. In use, the light source should be behind the glass article so that a reading at the second polarizer can be made. However, the clearance behind the glass article on a typical manufacturing line is usually only 2–4" (the minimum required for the motion of mechanical devices and the location of burners), far too narrow for the 10-inch depth of the light source of the available polariscopes.

It would be an advantage to have a polariscope that is usable on a glass article manufacturing line without removing the glass article and that overcomes the above-noted difficulties.

SUMMARY OF THE INVENTION

An object of the present invention is to provide a novel polariscope that is adapted to be hand-carried. Preferably, the polariscope weighs less than two pounds and does not require an external power source.

A further object of the present invention is to provide a novel polariscope that includes a lightweight, C-shaped housing with a sequential arrangement of a battery-powered LED light source, a first polarizer, a full wave plate at one distal end, and a second polarizer at a second distal end, where the housing includes a hand-grip that houses a battery and the battery is selectively connected to the LED light source with a switch carried on the hand-grip.

A yet further object of the present invention is to provide a novel LED polariscope having a sequential arrangement of light source, first polarizer and full wave plate at the first distal end that is less than two inches thick.

These and other objects and advantages of the invention will be apparent to those of skill in the art of the present invention after consideration of the following drawings and description of preferred embodiments.

BRIEF DESCRIPTION OF THE DRAWING

The Figure is a schematic view of the LED polariscope of this invention.

DETAILED DESCRIPTION OF THE INVENTION

For a better understanding of the present invention, together with other and further objects, advantages and capabilities thereof, reference is made to the following disclosure and appended claims taken in conjunction with the above-described drawing.

The present invention recognizes that the advantages of an LED polarimeter discussed in the above-cited application can be translated to a polariscope to overcome the disadvantages of the prior art. In particular, the LED light source is an efficient, low power device that generates a small amount of heat so that there is no damage to the polarizing film. A typical LED device consumes only 6 watts of power compared to 60–100 watts for an incandescent source and roughly 25 watts for a compact fluorescent source. Moreover, LEDs have long lifetimes (more than 60,000 hours) so that replacement may not be required, avoiding problems associated with color shifts in the light source.

Referring to the Figure, an embodiment of the LED polariscope of this invention includes a generally C-shaped support (or housing) 10 having two distal ends 12, 14 connected by a grip 16 that is arranged and adapted to be hand-held. At one distal end 12 is a sequential arrangement of a battery-powered LED light source 18, a first polarizer 20, and a full wave plate 22 (e.g., 560 nm). Second distal end 14 carries a second polarizer 24 that is spaced from the sequential arrangement at first distal end 12 and that is aligned with LED light source 18, first polarizer 20, and full wave plate 22 along a central axis 26. Grip 16 houses a battery 28 and a switch 30, such as a momentary contact switch, that selectively connects battery 28 to LED light source 18. An article whose stress is to be measured is placed between the two distal ends 12, 14 in order measure its birefringent properties.

The LED polariscope of this invention preferably weighs less than two pounds so that it is easily hand-carried and has a sequential arrangement of light source, first polarizer, and full wave plate that preferably is less than two inches thick (measured along the central axis) so that this sequential arrangement will fit over a glass article on a manufacturing line without removing the glass article from the line. The polariscope of the embodiment in the Figure has an overall size of 4"×7"×8" and weighs about 1.6 pounds.

The housing 10 may be made of a suitable lightweight material that retains a relative position of the two distal ends during operation of the polariscope. For example, the housing 10 may aluminum or plastic.

A distance between the two distal ends 12, 14 may be selectively adjustable by providing means for moving the distal ends in relation to each other along the central axis. For example, a length of the grip 16 may be adjustable, such as with a telescoping arrangement of tubes 16a, or the distal ends may be attached to the grip so as to be movable along the grip, such as in grooves (not shown) or the like. In addition, a length of distal ends 12, 14 that defines a distance between central axis 26 and grip 16 may be similarly adjustable (not shown).

LED light source 18 preferably yields a generally uniform illumination field of white light. An example of a suitable LED light source is OSRAM Opto Semiconductor ML/555Sq/OS/ML02A/W. This light source is flat, uses 40 LEDs to edge light a printed screen, and produces an even 2"×2" field of white light at about 1260 cd/m². Other suitable LED light sources may also be used. An advantage of this type of light source is that the light source and primary optics (the first polarizer and full wave plate) can be less than 2 inches thick; indeed in this particular embodiment these are only about an inch thick. Further, this type of light source can be powered with one or more batteries. For example, the above-mentioned light source can be powered with three 9 volt batteries that are easily housed in grip 16.

First and second polarizers 20, 24 each include a polarizing film, preferably with an extinction ratio of about 10,000:1 or greater. The first polarizer 20 is held in position relative to the full wave plate 22 such that the orientation of the first polarizer 20 is fixed with respect to the full wave plate 22. First and second polarizers 20, 24 are arranged as cross polars and full wave plate 22 is aligned so that the field of view becomes a magenta color. In this orientation, stress vectors that are 45° to the polarization direction of the polarizers will appear either yellow or blue, depending on whether they are tensile or compressive.

In an alternate embodiment, polariscope of this invention may be converted into a polarimeter by making the second polarizer 24 rotatable about the central axis 26 and using a monochromatic LED light source. In addition, the second polarizer 24 may be provided with indicia suitable for determining the degree of rotation.

While there have been shown and described what are present considered to be the preferred embodiments of the invention, it will be apparent to those skilled in the art that various changes and modifications can be made herein without departing from the scope of the invention as defined by the appended claims.

What is claimed is:

1. A polariscope comprising:
   a housing that is arranged and adapted to be hand-carried, said housing including,
   a sequential arrangement of a battery-powered LED light source, a first polarizer, and a full wave plate, the sequential arrangement is spaced from a second polarizer that is substantially aligned with said LED light source, said first polarizer and said full wave plate along a central axis,
   the LED light source providing a generally uniform illumination field of white light, the orientation of the first polarizer being fixed with respect to the full wave plate, the first and second polarizers being arranged as cross polars, the full wave plate being aligned so that the field of view is a magenta color, and
   a battery and a switch for selectively connecting said battery to said LED light source.

2. The polariscope of claim 1, wherein the polariscope weighs no more than two pounds.

3. The polariscope of claim 1, wherein said housing comprises a hand-grip between said sequential arrangement and said second polarizer and wherein said battery is inside said hand-grip.

4. The polariscope of claim 1, wherein a distance between said sequential arrangement and said second polarizer is adjustable.

5. The polariscope of claim 4 wherein said distance is adjustable by a telescoping arrangement of tubes.

6. The polariscope of claim 1, wherein said LED light source comprises plural LEDs that provide the generally uniform illumination field of white light.

7. The polariscope of claim 1, wherein said sequential arrangement is less than two inches thick, measured along the central axis.

8. The polariscope of claim 1, wherein said housing is C-shaped.

9. A polariscope comprising:
   a C-shaped support having at one distal end a sequential arrangement of a battery-powered LED light source, a first polarizer, and a full wave plate, and at a second distal end a second polarizer that is substantially aligned with said LED light source, said first polarizer and said full wave plate along a central axis;
   the LED light source providing a generally uniform illumination field of white light, the orientation of the first polarizer being fixed with respect to the full wave plate, the first and second polarizers being arranged as cross polars, the full wave plate being aligned so that the field of view is a magenta color;
   a battery and a switch for selectively connecting said battery to said LED light source; and
   said distal ends of said C-shaped support being connected by a grip that is arranged and adapted to be hand-held and that houses said battery and said switch.

10. The polariscope of claim 9, wherein the LED light source is comprised of multiple LEDs arranged to provide the generally uniform illumination field of white light.

11. The polariscope of claim 9, wherein the second polarizer and the full wave plate are moveable along the central axis.

12. The polariscope of claim 9 wherein a distance between said sequential arrangement and said second polarizer is adjustable by a telescoping arrangement of tubes.

* * * * *